(12) United States Patent
Gadde et al.

(10) Patent No.: US 7,459,139 B2
(45) Date of Patent: Dec. 2, 2008

(54) PROCESS FOR PREPARATION OF NON-HAZARDOUS BROMINATING AGENT

(75) Inventors: Ramachandraiah Gadde, Bhavnagar (IN); Pushpito Kumar Ghosh, Bhavnagar (IN); Adimurthy Subbarayappa, Bhavnagar (IN); Ashutosh Bedekar, Bhavnagar (IN); Dipak Balvantrai Shukla, Bhavnagar (IN)

(73) Assignee: Council of Scientific and Industrial Research, New Delhi (IN)

( * ) Notice: Subject to any disclaimer, the term of this patent is extended or adjusted under 35 U.S.C. 154(b) by 1326 days.

(21) Appl. No.: 10/449,723

(22) Filed: May 30, 2003

(65) Prior Publication Data

US 2004/0242939 A1 Dec. 2, 2004

(51) Int. Cl.
*C01B 11/20* (2006.01)
*C22B 26/10* (2006.01)

(52) U.S. Cl. .................... 423/475; 423/472; 423/499.1; 252/182.16; 252/187.2

(58) Field of Classification Search ................. 423/472, 423/475, 499.1; 252/182.16, 187.2
See application file for complete search history.

(56) References Cited

U.S. PATENT DOCUMENTS

| | | | |
|---|---|---|---|
| 4,650,658 A | | 3/1987 | Shiozawa et al. |
| 4,719,096 A | * | 1/1988 | Lesher et al. ............... 423/504 |
| 6,143,698 A | * | 11/2000 | Murphey et al. ........... 507/145 |
| 6,165,343 A | * | 12/2000 | Blum et al. ................. 205/556 |
| 6,365,786 B1 | * | 4/2002 | Ramachandraiah et al. . 568/726 |
| 2003/0136941 A1 | * | 7/2003 | Vohra et al. ............ 252/182.16 |

FOREIGN PATENT DOCUMENTS

| | | |
|---|---|---|
| IL | 84830 | 1/1995 |
| WO | 02 057207 | 7/2002 |

OTHER PUBLICATIONS

English Abstract of IL 84830 dated Jan. 24, 1995 Database WPI Section CH, Week 199517 Derwent Publications (XP 002268 916).

* cited by examiner

*Primary Examiner*—Ngoc-Yen M Nguyen
(74) *Attorney, Agent, or Firm*—Ladas & Parry LLP

(57) ABSTRACT

A cost-effective process is described for the preparation of a stable and non-hazardous brominating reagent containing 2:1 stoichiometric ratio of alkali bromide to alkali bromate. The process comprises of reacting alkaline bromine intermediate mixture, obtained from bromine recovery plant, with chlorine gas in the presence of a strong alkali to oxidize the bromide ions to bromate ions. This brominating reagent is useful for the bromination of aromatic compounds by substitutions.

7 Claims, No Drawings

PROCESS FOR PREPARATION OF NON-HAZARDOUS BROMINATING AGENT

FIELD OF THE INVENTION

The present invention relates to an improved process for the preparation of non-hazardous brominating reagent. This invention particularly relates to the preparation of brominating reagent from the alkaline intermediate bromide-bromate mixture obtained from bromine recovery plants. The reagent so obtained is convenient to handle, non-hazardous, easy to transport and can be effectively used in the preparation many aromatic bromo compounds.

BACKGROUND OF THE INVENTION

Liquid bromine is used to prepare a variety of brominated compounds through substitution reactions. This includes commercially important products such as i) tetrabromo-bisphenol-A (TBBPA)—a flame retardant, ii) eosin—a pigment used in personal care products, iii) bromoacetanilide—an analgesic and antipyretic agent, iv) tribromophenol—an intermediate used in the manufacture of antiseptic, germicide, fungicide, fire extinguishing fluids, fire retardant. and v) 2-bromo-4-nitro acetanilide—a drug intermediate used in the preparation of nimenslide. However, liquid bromine is hazardous by nature and requires extreme care in its production, transportation, and utilization. Besides this, special equipments are required to handle liquid bromine. Moreover, for substitution reactions depicted by equation 1, half of the bromine atoms end up in the effluent as hydrobromic acid.

$$R\text{—}H + Br_2 \rightarrow RBr + HBr \quad (1)$$

where R=aromatic substrate.

Reference is made to *Survey of Organic Syntheses*, Published by Wiley-Inter Science, New York, 1970, Chapter 7 by C. A. Buechler and D. E. Pearson who have reported the preparation of tribromophenol by the interaction of phenol with liquid bromine in a liquid phase. In this process more than 50% of bromine atom ends up as hydrobromic acid as byproduct. The main drawback of this method is the use of hazardous and corrosive liquid bromine. Further, it requires special equipments for handling the liquid bromine. The atomic efficiency of liquid bromine is only 50 percent.

U.S. Pat. No. 5,475,153 (1995) to S. Armstrong discloses the preparation of tetrabromobisphenol-A by reacting bisphenol-A with liquid bromine. Here, hydrogen peroxide was used as oxidizing agent to oxidize hydrobromic acid formed as byproduct to liberate bromine which will react with the unreacted bisphenol-A. The main drawback of this process is the use of hazardous and corrosive liquid bromine. Moreover, the addition of oxidizing agent will increase the unit operations as well as the reaction time.

Z. E. Jolles in his book entitled *Bromine and its Compounds*, Published by Ernest Benn Ltd., London, 1966, p 394 have reported the preparation of 3-bromomethyl-thiophene by adding 2 moles of N-bromosuccinimide to a separately prepared solution of (i) 2.24 moles of 3-methyl-thiophene; (ii) 0.0165 moles of benzoyl peroxide in 700 ml dry benzene and keeping the reaction mixture under stirring at reflux conditions. In this process, prior to recovery of the product by distillation of benzene, the reaction mixture after complete addition of succinimide is cooled below 5° C. The drawback of this process is that the reagent, N-bromosuccinimide is prepared using liquid brimine at temperature below 5° C. in highly alkaline solution. Cooling of reaction mixture below 5° C. also makes the process cost-intensive. Liquid bromine is corrosive and requires special device to handle it. Besides, benzene is carcinogenic and its recovery by distillation makes the process complicated and needs special care.

Brominating agents that are easy to handle are known but are used mainly for more selective transformations or those where bromine is less effective. A. Groweiss in *Organic Process & Development* 2000, 4, 30-33, discloses the preparation of active brominating species. In this process a strong acid viz. $H_2SO_4$ is slowly added to a stirred aqueous solution or slurry of the reagent containing stoichiometric quantity of sodium bromate and deactivating substituents like nitrobenzene; benzoic acid; benzaldehyde, 4-nitrofluorobenzene and 4-fluorobenzoic acid, while maintaining the temperature in the range of 40-100° C. The drawback of this process is that sodium bromate is costly and its use cannot be justified in more conventional bromination reactions that can be affected by liquid bromine as such. Moreover, the use of sulphuric acid and deactivating substituents are more prone to health hazard, at high temperature. Sulphuric acid is also corrosive in nature.

P. C. Merker et al (*J. Chem. Ed.* 26, 1949 p 613) have disclosed the preparation of p-bromoacetanilide by separately preparing a solution of acetanilide (0.232 moles) in cold glacial acetic acid and reacting this solution with pyridiniumbromideperbromide (0.12 moles) in 40 ml hot glacial acetic acid. The resultant mixture was allowed to stand for 30 minutes at room temperature, and then 2 ml of saturated sodium bisulfite solution was added to aqueous solution. The resulting mass was filtered, washed with water and finally recrystallized from hot 95% aqueous ethanol to yield p-bromoacetanilide. The drawbacks of this method are that the brominating agent requires liquid bromine and hydrobromic acid in its preparation which are corrosive and difficult to handle. (L. F. Fieser and M. Fieser, *Reagents for Organic Chemistry* Vol. 1, John Wiley, New York, 1967, p967) The reagent is costlier than liquid bromine. It involves multi steps making the process less cost benefit G. Rothenberg and J. H. Clark in *Organic Process & Development* 2000, 4, 270-274, have disclosed the catalytic bromination of aromatic compounds using alkali bromide or hydrobromic acid and hydrogen peroxide in the presence of 1-2 mol percent vanadium pentoxide catalyst. The drawbacks of this method are that more than stoichiometric quantities of hydrogen peroxide are required and the reaction needs a catalyst. Such catalytic protocols, in general, have several shortcomings like oxidative instability, high purification cost, strict pH and temperature controls. Besides, these reactions require stoichiometric amounts of metal to ensure satisfactory activity.

U.S. Pat. No. 5,817,888 (1998) to H. Y. Elnagar discloses a bromination process wherein organic compounds were selectively brominated in the para-position in high purity and yield. In this bromination process bromine chloride solution was used as brominating reagent which was slowly added at a controlled rate to a solution of aromatic compound maintained at a temperature around 0-4° C. under stirring. At the closure of the reaction, the reaction was quenched with few drops of saturated sodium sulfite solution and then diluted with normal organic solvents. The disadvantages of this method is that the preparation of brominating reagent, bromine chloride, still requires hazardous liquid bromine and chlorine gas under specified conditions.

Pending Application No. PCT/IB02/00386 dated Jan. 25, 2002 to G. Ramachandraiah et al reports the preparation of non-hazardous brominating reagent suitable for aromatic substitution reactions. In this method, calculated amounts of commercially available 4% hypochlorite solution was added to an industrial alkaline bromine mixture and allowed to stand for 24 h for completion of the desired reaction, optionally followed by evaporation to get brominating reagent in solid form. The drawbacks of this process are that, the volumes of hypochlorite solution required to achieve the desired bromide to bromate ratio, is large which unnecessarily increase the process cost or require large containers to handle bromination reactions. The reaction between bromide and hypochlorite and the subsequent reactions are slow as they are highly pH dependent. Further, the hypochlorite solution contains chlorate ions as an integral part in considerable levels, which being a strong oxidizing agent in acidic solutions, may take part in the bromination reactions and produce unwanted side products deteriorating the quality of the product.

OBJECTS OF THE INVENTION

The main object of the present invention is to provide an improved process for environmental benign brominating reagent which obviates the drawbacks as detailed above.

Another object of the present invention is to dispense the use of corrosive liquid bromine in the preparation of brominating reagent.

Still another object of the present invention is to prepare a brominating reagent from an aqueous alkaline bromine intermediate mixture obtained from bromine recovery plant.

Yet another object of the present invention is to increase the bromide:bromate ratio in the alkaline bromine mixture from 5:1 to 2:1 in order to maximize the bromine atom efficiency in aromatic substitution reactions.

Yet another object of the present invention is to provide a method wherein the bromine discharge in the effluent is minimized i.e. <0.5 percent.

Yet another object of the present invention is to purge inexpensive chlorine gas through alkaline bromine mixture that can oxidize bromide ions to bromate ions in alkaline medium to achieve a stoichiometry of 2:1 bromide to bromate ratio in the reagent.

Yet another object of the present invention is to obtain the brominating reagent in solid form which is easy to handle, storage and transport.

Yet another object of the present invention is to carry out the reactions at ambient temperature in the preparation of the brominating reagent of this invention.

SUMMARY OF THE INVENTION

The aim of the present invention is directed to provide an improved process for the preparation of a non-hazardous brominating reagent with active bromine content in the range 45 to 55 weight percent. The alkaline bromine intermediate mixture obtained from bromine recovery plant having bromide to bromate ratio in the range of 4:1 to 5:1 was used. The homogeneous mixture of alkaline bromine was purged with commercial chlorine gas in presence of an alkali. The overall 2:1 molar combination of bromide to bromate was then achieved in it by suitable dilution with fresh alkaline bromine mixture. During the oxidation and dilution process the temperature of the reaction was maintained between 20 to 40° C. The present process is rapid, safe and cost effective giving highly reactive brominating reagent which is easy to handle. The solid product is recovered by evaporation and it obviates the need for any further purification step. This brominating reagent is useful in bromination of various aromatic substrates to prepare organo-bromo compounds.

Accordingly, the present invention provides a process for preparing a non-hazardous brominating reagent by the oxidation of a source of bromide ions to bromate ions, comprising (i) dissolving an alkali in deionized water;
(ii) dispersing the source of bromide ions in 0.5 to 2.0 times v/v of deionized water;
(iii) purging chlorine gas or flue chlorine gas to the solution of step (ii) above at a rate ranging from 100 to 1000 ml per minute over a period of 6 to 8 hours or till brown colored vapors are evolved;
(iv) diluting the mixture with 2 to 3 times (v/v) of alkaline bromine mixture and the rest deionized water till a clear solution of the mixture is obtained;
(v) evaporating the mixture to obtain solid product, and drying the product at a temperature in the range of 55 to 80° C.;

In one embodiment of the invention the mixture of (i) and (ii) is stirred at 300 to 400 rpm in order to dissipate the heat generated during the dissolution of alkali salt.

In another embodiment of the present invention the source of bromide ions comprises an alkaline bromine intermediate mixture obtained from bromine recovery plant having bromide to bromate ratio in the range 4:1 to 5:1.

In another embodiment of the present invention, the alkali comprises caustic soda solution and is added to source of bromide ions in a concentration in the range of 2.5 to 2.8 moles per liter of total source of bromide ions.

In yet another embodiment of the present invention the temperature of the reaction mixture is in the range of 20 to 40° C.

In still another embodiment of the invention, the oxidising agent comprises chlorine gas or flue chlorine gas.

In yet another embodiment of the invention, the oxidizing agent is passed through the mixture of step (ii) at a rate in the range of 100 to 1000 ml per minute.

DETAILED DESCRIPTION OF THE INVENTION

The present invention provides a process for the preparation of an non-hazardous brominating agent from a source of bromide ions such as an alkaline bromine intermediate mixture obtained from bromine recovery plant.

According to the reaction (2) below, bromide ions can directly be oxidized to bromate ions in an alkaline medium. The acidic protons liberated in this reaction are neutralized (reaction 3) by the alkali present in it.

The final reaction mixture may be evaporated by known techniques to obtain the desired reagent in solid form.

According to the reaction 2 below, bromide ions can directly be oxidized to bromate ions in an alkaline medium. The acidic protons liberated in this reaction are neutralized (reaction 3) by the alkali present in it. The reaction 3 is governed by the quantity of alkali reddish yellow which is characteristic mark for the right conversion of bromide ion to bromate ion to the desired extent.

$$2Br^- + 6Cl_2 + 6H_2O \rightarrow 2BrO_3^- + 12H^+ + 12Cl^- \qquad (2)$$

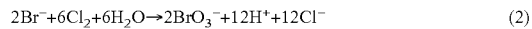

$$H^+ + OH^- \rightarrow H_2O \qquad (3)$$

In the present invention, the above said reactions were carried out in 5-10 liters round bottom flasks equipped with three necks and a cooling bath if necessary. Here, the alkaline bromine intermediate mixture obtained from bromine recovery plant based on "Cold process" preferably contains from about 18 to 25 wt % of bromide and from about 3 to 7 wt % of bromate and more preferably from about 20 to 22 wt % of bromide and from about 4 to 5 wt % of bromate, was used as a source of bromide ions. The oxidizing agent selected was a commercially available chlorine gas or effluent chlorine gas from any industry for example chlor-alkali industry.

In accordance with this invention, calculated amount of alkali was added to a predetermined volume of alkaline bromine mixture taken in a vessel having stirring facilities and maintaining the temperature at 20 to 40° C. Commercially available chlorine gas was purged through this homogeneous mixture at a regulated flow rate, for a period till brown colored vapours were evolved, while keeping the entire mass under stirring. The required bromide to bromate ratio in the oxidized solution was obtained by requisite dilution with fresh alkaline bromine mixture. Solid and easy to handle brominating reagent was obtained by evaporation of final reaction mixture, followed by drying and grinding to the desired size.

The dissolution of alkali in water is an exothermic reaction. It is thus, necessary to cool the vessel to maintain to room temperature during the preparation of alkali solution.

Since, the rate of bromide oxidation to bromate is fast in concentrated basic solutions, it is preferable to conduct the reaction by dissolving the alkali in minimum volumes of alkaline bromine and deionised water so as to get the required quantity of bromide conversion and then diluting with suitable quantity of original alkaline bromine mixture to adjust the bromide and bromate ratio 2:1.

In the preparation of brominating reagent, the reaction temperature preferably ranges from about to 15 to 75° C. and more preferably are at about ambient temperature (i.e. about 20 to 40° C.). Reaction rates are usually rapid even below ambient temperature and at atmospheric pressure.

The brominating reagent was characterized by determining its bromate and bromide contents by estimating liberated bromine, spectrophotometrically (K. Kumar and D. W. Margerum, *Inorg. Chem.* 1987, 26, 2706-2711) by measuring the absorbance at 390 nm and using the appropriate molar extinction coefficient ($\epsilon$, 167 $M^{-1}$ $cm^{-1}$ in absence and 522 $M^{-1}$ $cm^{-1}$ in the presence of large excess of bromide). The standard iodometric volumetric method (A. I. Vogel *A text book of Quantitative Inorganic Analysis*, 3rd Ed. Longman, 1962, p349) was followed to estimate for bromate ions and total bromine content.

The present invention relates to the preparation non-hazardous and stable brominating reagent suitable for various applications. This brominating reagent was prepared from alkaline intermediate bromine mixture by oxidation process using chlorine gas at ambient temperature. The water-soluble solid reagent can be efficiently used for aromatic substitution reactions wherein maximum bromine atom efficiency can be achieved. The method of the present invention does not require any special devise and the use of hazardous and corrosive liquid bromine is dispensed. In the present invention alkaline intermediate bromine mixture obtained from bromine recovery plants was utilized to prepare solid brominating reagent having high atom efficiency. The inventive steps adopted in the present invention are (i) preparing non-hazardous brominating reagent from intermediate mixture obtained from bromine recovery plant which obviates the need of liquid bromine; (ii) the reagent is prepared in the ambient temperature (20-40° C.) and does not require cooling below 5° C.; (iii) commercially available and/or flue chlorine gas is used for the oxidation of bromide ion to bromate ion; (iv) the volumes of alkaline bromine mixture is reduced by dispensing the use of other oxidants in solution; (v) dilution is affected using deionized water and the need for organic solvents is dispensed.

The following examples are given by way of illustrations and therefore should not be construed to limit the scope of the present invention.

EXAMPLE 1

Alkaline bromine mixture (1.0 liter) having bromide to bromate ratio 4.4:1 was taken in three necked round bottom flask to which 2.0 liters of deionised water having 13.05 moles of NaOH was mixed at 25° C. under stirring. This reaction mixture was purged with chlorine gas at a rate of 300 ml per minute while maintaining the temperature at 25° C. and continuing the purging of chlorine gas till brown colored vapors were evolved. The passing of chlorine gas was stopped and the reaction mixture was transferred to another vessel where it was diluted with 4.0 liters of alkaline bromine mixture and 0.5 liter of deionised water keeping the entire mass under stirring and continued for another 10 minutes. The solid brominating reagent so formed having bromide to bromate ratio 2:1, was separated by evaporating the water by known techniques and drying the product at 70° C. The active bromine content was found to be 45.3%.

EXAMPLE 2

3.0 liter of alkaline bromine mixture having bromide to bromate ratio 4.4:1 was taken in three necked round bottom flask to which 3.5 liters of deionised water having 26.10 moles of NaOH was mixed at 30° C. under stirring. This reaction mixture was purged with chlorine gas at a rate of 300 cc per minute while maintaining the temperature at 30° C. and continuing the purging of chlorine gas till brown colored vapors were evolved. The passing of chlorine gas was stopped and the reaction mixture was transferred to another vessel where it was diluted with 7.0 liters of alkaline bromine mixture and 0.5 liter of deionised water keeping the entire mass under stirring and continued for another 10 minutes. The solid brominating reagent so formed and having bromide to bromate ratio 2:1 was separated by evaporating the water by known techniques and drying the product at 70° C. The active bromine content was found to be 50.3%.

EXAMPLE 3

3.0 liter of alkaline bromine mixture having bromide to bromate ratio 4.4:1 was taken in three necked round bottom flask to which 3.5 liters of deionised water having 26.10 moles of NaOH was mixed at 38° C. under stirring. This reaction mixture was purged with chlorine gas at a rate of 300 cc per minute while maintaining the temperature at 38° C. and continuing the purging of chlorine gas till brown colored vapors were evolved. The passing of chlorine gas was stopped and the reaction mixture was transferred to another vessel where it was diluted with 7.0 liters of alkaline bromine mixture and 0.5 liter of deionised water keeping the entire mass under stirring and continued for another 10 minutes. The solid brominating reagent so formed and having bromide to bromate ratio 2:1 was separated by evaporating the water by known techniques and drying the product at 70° C. The active bromine content was found to be 50.3%.

EXAMPLE 4

3.0 liter of alkaline bromine mixture having bromide to bromate ratio 4.4:1 was taken in three necked round bottom flask to which 3.5 liters of deionized water having 26.10 moles of NaOH was mixed at 28° C. under stirring. This reaction mixture was purged with chlorine gas at a rate of 900 cc per minute while maintaining the temperature at 28° C. and continuing the purging of chlorine gas till brown colored vapors were evolved. The passing of chlorine gas was stopped and the reaction mixture was transferred to another vessel where it was diluted with 7.0 liters of alkaline bromine mixture and 0.5 liter of deionised water keeping the entire mass under stirring and continued for another 10 minutes. The solid brominating reagent so formed and having bromide to bromate ratio 2:1 was separated by evaporating the water by known techniques and drying the product at 70° C. The active bromine content was found to be 55.0%.

EXAMPLE 5

To 5.0 ml of dichloromethane containing 4-nitroaniline (1 g, 7.246 m mole) in a 250 ml round bottom flask, 1.45 ml of 12 N hydrochloric acid and 10 ml of deionised water were added. To this reaction mixture, brominating reagent containing (2.9 g) of brominating reagent dissolved in 20 ml of deionised water was added slowly under continuous stirring at 28° C. for a period of 30 to 45 minutes. After completion of the addition, stirring was continued for another 15 minutes. The organic layer was separated and extracted with dichloromethane. The organic layer and the organic extracts were mixed and then washed successively with sodium thiosulphate solution and brine. The product, 2,6-dibromo-4-nitroaniline was dried over anhydrous sodium sulphate and concentrated to yield 98.7%. It was characterized by melting point; NMR; IR and elemental analysis.

The main advantages of the present invention are
1. Environmentally benign brominating reagent can be prepared from alkaline intermediate bromine mixture which dispenses the use of liquid bromine.
2. Chlorine gas and/or flue chlorine gas can be used as an oxidizing agent which obviates the need of other costly oxidizing agent, hypochlorite and the impurity, chlorate in it.
3. The bromide ion present in the intermediate mixture can be oxidized at ambient temperature.
4. The aromatic substitution using this reagent can be carried out with high atomic efficiency.
5. This reagent is safe to handle, can be easily transported and preserved.

We claim:
1. A process for preparing a brominating reagent by the oxidation of a source of bromide ions to bromate ions, comprising
   (i) dissolving an alkali in de-ionized water to form an alkali solution
   (ii) mixing a source of bromide ions with the alkali solution to form a reaction mixture
   (iii) purging the reaction mixture with chlorine gas or flue chlorine gas at a rate of 100 to 1000 ml per minute for 6 to 8 hours to provide a purged reaction mixture
   (iv) diluting the purged reaction mixture with 2 to 3 times v/v of the source of bromide ions to provide a diluted purged reaction mixture
   (v) evaporating water from the diluted purged reaction mixture to obtain a solid brominating reagent and drying the solid brominating reagent at a temperature in the range of 55 to 80° C.

2. A process as claimed in claim 1 wherein the source of bromide ions comprises an alkaline bromine intermediate mixture obtained from a bromine recovery plant having a bromide to bromate ratio in the range 4:1 to 5:1.

3. A process as claimed in claim 1 wherein the alkali solution comprises a caustic soda solution and is added to the source of bromide ions in a concentration in the range of 2.5 to 2.8 moles per liter of the source of bromide ions.

4. A process as claimed in claim 1 wherein the temperature of the reaction mixture is in the range of 20 to 40° C.

5. A process according to claim 1 wherein the chlorine gas or flue gas oxidizes the bromide ions to bromate ions to produce a ratio of bromide ions to bromate ions in the range of 2:1 in the diluted purged reaction mixture.

6. A process as claimed in claim 1 wherein the purged reaction mixture is diluted with 2 to 3 times v/v of the source of bromide ions to provide a bromide ion to bromate ion ratio in the range of 1.9:1 to 2.2:1.

7. A process as claimed in claim 1 wherein the solid brominating reagent has an active bromine content of between 45 to 55 percent.

* * * * *